(12) United States Patent
Flechsig et al.

(10) Patent No.: US 9,823,215 B2
(45) Date of Patent: Nov. 21, 2017

(54) ELECTROCHEMICAL SENSOR

(75) Inventors: Gerd-Uwe Flechsig, Teterow (DE);
Anne Walter, Bentwisch (DE); Martin Jacobsen, Rostock (DE)

(73) Assignee: Gensoric GmbH, Rostock (DE)

( * ) Notice: Subject to any disclaimer, the term of this patent is extended or adjusted under 35 U.S.C. 154(b) by 805 days.

(21) Appl. No.: 14/236,997

(22) PCT Filed: Aug. 1, 2012

(86) PCT No.: PCT/EP2012/065066
§ 371 (c)(1),
(2), (4) Date: Jul. 18, 2014

(87) PCT Pub. No.: WO2013/017635
PCT Pub. Date: Feb. 7, 2013

(65) Prior Publication Data
US 2014/0326618 A1 Nov. 6, 2014

(30) Foreign Application Priority Data
Aug. 4, 2011 (DE) .................. 10 2011 109 402

(51) Int. Cl.
*G01N 27/327* (2006.01)

(52) U.S. Cl.
CPC ..... *G01N 27/3275* (2013.01); *G01N 27/3276* (2013.01)

(58) Field of Classification Search
CPC .................................. G01N 27/3275
See application file for complete search history.

(56) References Cited

U.S. PATENT DOCUMENTS

2008/0269066 A1* 10/2008 Flechsig ............ C12Q 1/6837
506/9

FOREIGN PATENT DOCUMENTS

| DE | 10 2004 017 750 A1 | 4/2004 |
| DE | 10 2005 007 148 B4 | 2/2005 |
| WO | WO 01/83674 A1 | 11/2001 |
| WO | WO 2007/020093 A2 | 2/2007 |

OTHER PUBLICATIONS

Grundler et al., "Review: Principles and Analytical Applications of Heated Electrodes" Microchim Acta 154, pp. 175-189 (2006).*
Wikipedia "Drop (liquid)" accessed from https://en.wikipedia.org/wiki/Drop_(liquid) on Sep. 21, 2016.*
(Continued)

*Primary Examiner* — Bryan D. Ripa
(74) *Attorney, Agent, or Firm* — Meunier Carlin & Curfman LLC (57) ABSTRACT

This invention relates to an electrochemical sensor (1), comprising a base element (3), which is made of electrically insulating material and has a planar surface (9), and a pair of conductors (5), which are attached to said planar surface (9) of the base element (3), wherein the two conductors (5) of the pair are connected by at least one wire-shaped electrochemical working electrode (7). The invention further related to a sensor array (21), which has several previously described sensors (1), and to a method for coating a working electrode (7) of the previously described sensor (1).

26 Claims, 4 Drawing Sheets

(56) References Cited

OTHER PUBLICATIONS

"Theory and Practice of Sensors with Hot-Wire Electrodes" by P. Grundler Fresenius J. Anal. Chem. 362, pp. 180-183 (1998).*
"DNA Hybridization Detection at Heated Electrodes" by Flechsig et al., Langmuir 21, pp. 7848-7853 (2005).*
Flechsig, et al., "DNA Hybridization Detection at Heated Electrodes" Langmuir 2005, American Chemical Society, pp. 7848-7853.
Jacobsen, et al., "Directly Heated Bismuth Film Electrodes Based on Gold Microwires" Electroanalysis vol. 22, No. 13, pp. 1483-1488, 2010.
Grundler, et al., "Deposition and Stripping at Heated Microelectrodes. Arsenic (V) at a gold electrode" Electrochimica Acta vol. 43, No. 23, pp. 3451-3458, 1998.
Beckmann, et al., "Modeling Hot Wire Electrochemistry, Coupled Heat and Mass Transport . . . " Journal of Physical Chemistry, vol. 104, pp. 764-769, 2001.
Wachholz Dissertation 2009 "Geheizte elektrochemische Sensoren mit neuartigen Arbeitselektroden und Heizgeneratoren" Rostock, 2009.
Wachholz, et al., "Template-Free Galvanic Nanostructuring of Gold Electrodes for Sensitive Electrochemical Biosensors" Electroanalysis vol. 21, pp. 2153-2159, 2009.

\* cited by examiner

ELECTROCHEMICAL SENSOR

The present invention relates to an electrochemical sensor having a base element made of electrically insulating material with a planar surface, and a pair of conductors which are superimposed on this planar surface of the base element, wherein the two conductors of the pair are connected by means of at least one wire-shaped electrochemical working electrode. Further, the present invention relates to a sensor array having a plurality of previously described sensors, and a method for coating a working electrode of a previously described sensor.

Sensors of this kind can be used for analyzing different liquids. As a result of an electrochemical reaction of certain constituents of the liquid at the surface of the working electrode or the coating thereof, the electrolysis current which flows through the surface of the working electrode and which can be measured within the scope of voltammetry or amperometry changes allowing conclusions to be drawn relating to the reaction which has taken place and therefore to a certain constituent of the liquid. Examples of such constituents can be DNA, RNA and also mercury, arsenic, cadmium or phenol derivatives or many other electrochemically active substances.

WO 2007/020093 teaches basic principles of the electrochemical detection of DNA hybridization on a gold electrode surface, e.g. with the help of osmium bonds. DE 10 2005 007 148 A1 describes an analysis method for nucleic acids which modifies the classical polymerase chain reaction (PCR) in such a way that the various steps are carried out on differently heated reaction surfaces, as a result of which simultaneous analysis and duplication are possible.

Devices for DNA hybridization on directly heated electrodes are described in Flechsig et al., 2005, Langmuir 21, 7848-7843. In particular, FIG. 1 of this publication shows a sensor according to the prior art, with which, with the help of a plastic bar, a working electrode can be coated with a few microliters of a nucleic acid solution to subsequently enable a hybridization of complimentary nucleic acids. Typically, particularly in the case of nucleic acid analysis, large quantities of the coating solution are not available, thus ruling out a free immersion of the electrode in such a solution.

However, the solution taught in Flechsig et al, 2005, has the disadvantage that a plastic bar has to be fitted into the device in order to deposit the drop of coating liquid thereon such that it wets the whole surface of the wire-shaped electrode. On the other hand, in benefiting from the advantages of the sensor, the person skilled in the art is faced with the task of finding a structurally simpler solution which, however, enables a uniform coating of the electrode even with a small volume of a coating solution.

This problem is solved by the present invention, in particular by the subject matter of the claims. In particular, the invention provides an electrochemical sensor (1) containing:
- a base element (3) made of electrically insulating material with a planar surface (9), and
- a pair of conductors (5) which are superimposed on this planar surface (9) of the base element (3), wherein the two conductors (5) of the pair are connected by means of at least one preferably wire-shaped working electrode (7), wherein a recess (11) is formed in this planar surface (9) of the base element (3) beneath the working electrode (7), wherein the bottom (13) of the recess (11) is at a distance from the working electrode (7).

Preferably, the recess is designed such that, when a liquid drop is introduced into the recess, the working electrode can be wetted by the liquid, wherein preferably the whole surface of the working electrode can be wetted. A uniform wetting is advantageous for the analysis, as the whole surface of the electrode can be coated.

Here, use is made of the fact that, due to the surface tension of the liquid, the liquid drop projects in the form of an arc out of the recess, i.e. beyond the plane in which the surface of the base element lies. In this way, for example, a wire-shaped working electrode which extends at approximately the level of the surface of the base element can be completely surrounded by the liquid. The recess can also be used to fix the liquid drop in a fixed position on the base element.

A liquid drop which is introduced into the recess and which completely surrounds the working electrode can be used to coat the working electrode with probes or microstructures for example. This coating process generally takes place before the actual analysis of a liquid. In doing so, the coating substances, as constituents of the coating liquid of the liquid drop, bond to the surface of the working electrode and form a layer, e.g. of probe molecules, which may be structured. After the liquid drop has been removed from the working electrode once more, the analysis of an analysis liquid which includes the target molecules can be carried out. Methods for coating and analysis are disclosed, for example, in WO 2007/020093 or DE 10 2005 007 148.

It is preferred when the liquid drop has a volume of 5 to 50 μL, preferably of 10 to 30 μL, or 15 to 20 μL. This size of drop enables extremely effective coating. A smallest possible quantity of coating liquid is required, wherein, however, sufficient coating substances, such as probe molecules or microstructures for example, can be deposited on the working electrode. It is preferred when the recess is designed such that the liquid drop surrounds the surface of the working electrode over its whole length.

In an embodiment of the invention, the sensor incorporates a liquid drop which has contact with the working electrode and with the bottom of the recess. This liquid drop preferably contains nucleic acids, e.g. a DNA probe, which can be at least partially single-stranded. Alternative probe molecules for an immunochemical sensor can be antibodies.

Further, the design according to the invention of the sensor has the advantage that, in the course of later measurements, the liquid can flow between the working electrode and the bottom of the recess and therefore freely circulate around the whole circumference of the wire-shaped working electrode so that its whole surface is available as a reaction surface.

In conjunction with the present invention, the surface of the working electrode is understood to mean the sleeve surface of the working electrode from the contact point of the working electrode with one of the conductors of a pair as far as the opposite contact point of the working electrode with the other conductor of the pair of conductors. The contact points of the working electrode with the conductors are designed such that an electrically conducting connection exists between the working electrode and the conductors. According to the invention, a solder, adhesive or clamp connection can be considered.

The conductors are preferably insulated with respect to the environment up to and including the contact points, so that, on the base element, only the working electrode is exposed to the environment, wherein the surface thereof can therefore come directly into contact with a liquid.

The working electrode preferably extends substantially in a straight line and in a plane parallel to the surface of the base element, preferably substantially in a plane with the surface of the base element. The recess in the base element is located substantially beneath the working electrode such that it is at a distance from the base element. The recess can have a round or also an elongated extension which can run substantially parallel to the working electrode. At the same time, the projection of the working electrode on the base element preferably lies on the center line of the recess.

In a further embodiment, the working electrode can be heated, in particular directly heated. In order to be able to carry out electrochemical measurements at increased temperatures, the electrode can be heated by means of water or the electrolyte as heat exchangers. Here, the whole quantity of the electrolyte is heated at the same time. This is disadvantageous, as firstly a large quantity of electrolyte is required, secondly temperature changes take place very slowly, and thirdly sensitive substances in the electrolyte solution can be affected. Heated electrodes, which, for example, are to be heated directly or indirectly by means of alternating or direct current, can also be used.

In the case of indirect heating, the working electrode can be constructed from a plurality of concentric layers which are galvanically separated from one another, wherein the outermost layer serves as an electrode and an inner layer as the heating wire. Indirect heating by means of heaters which are galvanically separated from the electrode is disadvantageous, as the structure of the sensors is complicated, the temperature changes usually take place more slowly on account of the thermal inertia, and the possibilities of miniaturization are restricted. Different directly heatable working electrodes, with which the heating current and the current for the electrochemical measuring signal flow together through the same conductor, are disclosed in the prior art.

According to the prior art, direct electrical heating of the working electrode and simultaneous fault-free electrochemical measurement can be made possible by a so-called symmetrical arrangement or special filter circuits. A variant of the directly heated working electrode has a third contact for connecting to the electrochemical measuring instrument exactly in the center between the two contacts for feeding-in the heating current. This arrangement eliminates troublesome effects of the heating current on the measuring signals. Of disadvantage here are, above all, the complex construction with three contacts per working electrode, the thermal disturbance due to the heat-dissipating third contact, and the more difficult miniaturization. In a preferred variant according to the invention, a symmetrical connection by means of a bridge circuit, which enables direct heating to be carried out, is therefore provided (Wachholz et al., 2007, Electroanalysis 19, 535-540, in particular FIG. 3; Dissertation Wachholz 2009).

Here, the sensor is preferably designed such that the temperature distribution at the surface of the working electrode is uniform. DE 10 2004 017 750 teaches, for example, an array having at least one working electrode superimposed on a carrier, which working electrode can be brought to its own temperature, wherein it is possible to keep the temperature distribution of the electrode surface uniform. This has significant advantages in the analysis of DNA sequences, for example. The methods used in this publication can also be used within the framework of the present invention. In particular, it is preferred that the conductors and the contact points between conductors and working electrode are electrically insulated with respect to the environment.

In a preferred embodiment, the conductors and the contact points of the conductor with the working electrode are covered by an electrically insulating layer on the sides which are not superimposed on the base element. Preferably, this layer is stable at least in a temperature range of 0° C. to 97° C., in particular of 20° C. to 93° C. In particular, the layer can be a laminating foil. Laminating foils are usually stable in the stated temperature range.

In this way, on the base element, only the working electrode can come into electrical contact with the liquid. When analyzing a liquid for example, the base element can therefore be completely covered by the liquid without the liquid coming into unwanted electrical contact, e.g. with the conductor. Only the working electrode itself comes into contact with the liquid, so that only the reactions at the surface of the working electrode are measured electrochemically.

Hot sealing adhesive, epoxy resin, polyester resin, silicone adhesive, solder resist varnish, dope, paraffin, rubber, PVC, Duroplast, PU resin, PTFE, PE, PS, polycarbonate, glass, oxides, nitrides or other organic or inorganic polymers, varnish-like, crystalline or amorphous materials can also be used as the insulating layer instead of laminating foils. The important thing is that the material of the insulating layer is temperature-stable between 0° C. and 97° C., in particular between 20° C. and 95° C. or between 25° C. and 93° C., as the temperature of the liquid preferably varies in this range during the analysis. Stable means that form and insulation properties are substantially constant. A small expansion or similar is possible, but should be reversible in the event of a temperature change.

A surprising advantage of the arrangement according to the invention of the working electrode above a recess in the base element without direct contact therewith along the recess relates to the case where the working electrode is heated. The inventors have recognized that an energy loss at the base element and also a high thermal inertia of the working electrode otherwise lead to a non-uniform temperature field of the working electrode and imprecise measuring results when analyzing the liquid. The recess prevents heat being dissipated from the base element and therefore, on the one hand, the working electrode being lost and, on the other, slower heating and cooling being the consequence.

On the one hand, the working electrode is heated in order to achieve an optimum reaction temperature depending on the constituent of the liquid which is to be detected, wherein the analysis process becomes more effective and/or more selective. If, for example, a hybridization of nucleic acids is to take place, then—as disclosed in the prior art—there is an optimum temperature for a specific accretion of complimentary nucleic acids. A denaturing in individual strands, which, for example, enables the analytes to be separated and therefore the sensors to be regenerated, typically takes place at high temperatures, e.g. at 93°-97° C. Further, a heating of the working electrode leads to thermal convection currents in the liquid surrounding the working electrode, which likewise makes the analysis process more effective.

In a preferred embodiment, the base element is a printed circuit board and the conductors are in the form of conductor tracks, wherein the conductors and the contact points of the conductor with the working electrode are covered by an insulating laminating foil on the sides which are not superimposed on the base element. The printed circuit board can be made of silicon and have a thickness of 1-2 mm for example. Here, the conductor tracks are preferably dosed into or vapor-deposited onto the printed circuit board. The conductor tracks can contain or be made of copper. Bonding, soldering, gluing or welding, for example, can be considered for the fixing method for the working electrode. The working electrode can be brought into contact with the conductor tracks and fixed thereto by means of vapor-deposited gold pads.

Within the framework of the invention, the working electrode is preferably a wire-shaped electrode. It preferably has a circular cross section. However, other cross-sectional shapes, such as for example triangular, rectangular or hexagonal cross-sectional shapes, or also various helical cross sections are also conceivable. The cross section can be constant over the length of the electrode. Changes in cross section over the length of the working electrode with respect to the diameter or cross-sectional shape are likewise conceivable. Wire-shaped electrodes in the form of individual fibers can also be used within the meaning of the present invention, as can other cross sections disclosed in the prior art. A preferred cross section is round, preferably with a diameter of approx. 10-50 µm, preferably approx. 20-30 µm, or in particular 25 µm. The resistance of the working electrode is at least 0.5 ohms, preferably approx. 1 ohms, but less than 20 ohms, preferably less than 10 ohms.

The working electrode can, for example, be made of gold, silver, copper, platinum, iridium, palladium, bismuth, antimony and/or carbon, in particular of gold, platinum and/or silver. Preferably, the working electrode is a gold wire. For example, a thermally robust platinum wire with a relatively high resistance can be provided with a thin gold layer in order to deposit thiol-linked SAMs (self-assembling monolayers). The working electrode can be coated with a mercury or amalgam film or with a solid metal film, e.g. made of bismuth, silver, gold or an alloy thereof. A coating with bismuth or mercury (in particular an amalgam film) can be used in order to reduce the hydrogen overvoltage.

Micro and/or nanostructures can also be present on the surface of the working electrode in order to increase the active electrode surface area and/or to improve the access of the analyte. Galvanic silver or gold structures, carbon nanotubes, fullerenes or graphemes are preferably used for this purpose. Methods for coating with nanostructures are described, for example, in Wachholz et al., 2009, Electroanalysis 21, 2153).

One of the stated coatings can be combined with a modification of the surface, e.g. with nucleic acids such as DNA probes; however, this is not necessary depending on the area of application. As described in the prior art, a modification with nucleic acids can be covalent or non-covalent. In particular, DNA probes linked by means of thiol groups can be superimposed on the surface of the working electrode(s), e.g. made of gold.

In a preferred embodiment, the working electrode has a length of approximately 3 to approximately 7 mm, preferably of approximately 5 mm, and a diameter of 10 to 50 µm, preferably 20 to 30 µm or of approximately 25 µm. On the one hand, when coating the working electrode with the help of a liquid drop with a volume of 5 to 50 µL, preferably of 10 to 30 µL, or of 15 to 20 µL, these dimensions of the working electrode enable an ideal distribution of the coating liquid around the surface of the working electrode and therefore an effective coating process. On the other hand, a working electrode of these dimensions provides an adequate number and accuracy of measuring results with, at the same time, the smallest possible size, which benefits an array arrangement of the sensor.

In an embodiment, the bottom of the recess is designed to be planar and parallel to the planar surface of the base element. The edge of the recess can be square, rectangular, round or ellipsoid, for example. The shape of the recess can guarantee a consistent, central position of the liquid drop. In another embodiment, the bottom of the recess is rounded, e.g. in a form which guarantees a consistent spacing of the bottom from the working electrode. A round, e.g. spherical or cylindrical-section-shaped form, of the recess is therefore also conceivable.

In the production of the sensor, the recess can be milled out, e.g. beneath the working electrode, which enables easy and automatable production.

In a preferred embodiment, the distance of the working electrode from the bottom of the recess at least one point, e.g. in the case of a planar bottom, or at all points, is a depth of 0.2 mm to 0.8 mm, preferably of 0.5 mm, wherein the recess preferably extends over the whole length of the working electrode. Such a spacing of the working electrode from the bottom of the recess enables sufficient flow around the working electrode with minimum size. The spacing is also ideal for the coating of a working electrode with a length of 3 to 7 mm, preferably of 5 mm, and a diameter of 20 to 30 µm, preferably of 25 µm, with a liquid drop of 5 to 30 µL, preferably of 10 to 20 µL, as the liquid drop surrounds the working electrode in an optimum form.

Further, the sensor or the sensor array can include at least one common counter electrode and/or at least one common pseudo reference electrode for sequential electrochemical readout. Alternatively, dedicated reference and counter electrodes can be provided for each working electrode for parallel (simultaneous) electrochemical readout. Preferably, an unheated carbon, gold or platinum electrode of any design is provided as the counter electrode. An unheated silver, gold or platinum electrode is preferred as the pseudo reference electrode. Reference and/or counter electrode can be arranged on the same base element or separately.

The preferred position of the pseudo reference electrode is located on the bottom of the recess, (in each case) beneath the heated working electrode(s), as this region is least affected by the thermal convection and most likely retains a constant temperature, which is important for a constant potential of the reference electrode. The counter electrode can also be arranged on the bottom of the recess.

In order to promote the effect of thermal convection flow, the sensor preferably includes a cooling device which is arranged opposite the working electrode away from the base element and which recools the liquid heated by the heated working electrode during the analysis process and therefore causes a circulation flow of the liquid, which in turn supports a reaction of the target molecules with the probe molecules. The cooling device preferably comprises a passive heat sink or an active Peltier cooler which covers the liquid with respect to the base element and thus encloses it between base element and cooler. Here, the underside of the cooler can be coated with gold or platinum or some other electrochemically inert material and preferably serves as the common counter electrode.

A significant advantage of the sensor according to the invention compared with the solution taught in Flechsig et al., 2005, is that the sensor arrangement can be extended easily and with little space requirement to form an array comprising a multiplicity of, if applicable, selectively heatable wire-shaped working electrodes.

A further advantage is that a relatively small amount of electrolyte is required to accommodate the reference and counter electrode of the electrochemical measuring cell. In addition, working electrode, counter electrode and reference electrode can be accommodated together and in a space-saving manner on such an array.

A further aspect of the present invention therefore relates to a sensor array which has two or more sensors according to the invention, wherein the sensors are preferably arranged on a common base element. As a result of the size of the sensors, which is as small as possible, a multiplicity of sensors can be arranged closely behind one another and/or next to one another on a common base element. The conductor tracks are preferably arranged lying close to one another in a parallel and/or symmetrical manner and are sealed together under an insulating layer. When analyzing a liquid, the whole surface area of the base element with all working electrodes mounted thereon is surrounded by the liquid.

In an embodiment, the recesses beneath at least 2 working electrodes of the sensor array are connected to one another to form a common channel. Alternatively or in addition, the recesses beneath at least 2 working electrodes can be separate from one another.

A common channel is particularly useful when the working electrodes above this channel are to be provided with the same coating, e.g. with the same nucleic acid probe. A liquid drop, which should be sized according to the dimensions of the channel and the number of working electrodes above it, can then be used for coating. This makes it possible, in a later analysis, to carry out parallel check measurements, for example, or, with the same coating or probe, to use different temperatures to which the working electrodes are heated and/or different materials of the working electrodes.

When working electrodes of a sensor array are arranged above separate recesses, they can of course also be provided with the same coating, e.g. with the same nucleic acid sequence. Alternatively, different coatings can be chosen, e.g. different nucleic acid sequences. Preferably, the working electrodes of a sensor array are arranged parallel to one another, in particular working electrodes above a common channel. Other arrangements are however conceivable.

In an embodiment, the working electrodes of the sensor array in each case have the same or more than one different material, wherein the material is selected from the group comprising gold, silver, mercury, copper, platinum, iridium, palladium, bismuth, antimony, carbon or combinations thereof. The use of different materials for different working electrodes can, for example, allow a plurality of constituents in a liquid to be detected simultaneously.

In an embodiment, the sensor array comprises a plurality of groups of working electrodes, wherein each group has a different material, however the individual working electrodes of a group have the same material. In another embodiment, the sensor array comprises a plurality of groups of working electrodes, wherein the individual working electrodes of the group have different materials, but each group has the same materials in each case.

In an embodiment, the sensor array has at least one sensor with a heated working electrode, wherein it preferably has a plurality of sensors with working electrodes which can be heated independently of one another in each case.

Depending on the material of the particular working electrode or superimposed probes and the specific constituent of the liquid (the analyte or the target molecule) to be detected, the temperature of each working electrode, which is individually optimum for a reaction of the specific target molecules of the liquid with defined probe molecules at the surface of the working electrode, can be provided by means of such a sensor array with selectively heatable working electrodes.

Further, the sensor array preferably includes at least one unheated counter electrode and/or optionally at least one unheated pseudo reference electrode.

A further aspect of the present invention relates to a method for coating a working electrode which comprises steps in which a liquid drop of a coating liquid is introduced into at least one recess of a sensor or sensor array according to one of the preceding aspects of the invention.

Here, a liquid drop with a volume of 5 to 30 µL, particularly preferably of 10 to 20 µL, is introduced into a recess which is formed such that the surface of a working electrode with a length of preferably 3 to 7 mm, particularly preferably of 5 mm, and a diameter of 10 to 30 µm, particularly preferably of 25 µm, is completely surrounded by the liquid drop. At the same time, it is also preferred when the distance of the working electrode from the bottom of the recess at least one point is a depth of 0.2 mm to 0.8 mm, preferably of 0.5 mm, and the recess extends over the whole length of the working electrode.

In this way, the probe molecules or micro or nano-structure-forming constituents or other constituents of the coating liquid which are provided for coating the working electrode can reach the whole surface of the working electrode and accumulate there uniformly. When this accumulation is complete, the rest of the coating liquid can be removed from the recess, and the working electrode can be used to analyze a sample solution, wherein certain constituents of the liquid, so-called target molecules, can bond with the probe molecules of the coating of the working electrode and thus give rise to a measurable current or voltage change (depending on the method: voltammetry, amperometry, coulometry, potentiometry) which in turn guarantees that conclusions can be drawn regarding the presence of the particular constituents.

However, probe molecules are only necessary in the case of immunochemical sensors and nucleic acids, e.g. DNA sensors. Heavy metal ions or smaller organic molecules are transferred directly at the working electrode, if necessary after prior enrichment (stripping voltammetry, chronopotentiometry, chronocoulometry).

Within the framework of the invention, "one" means "at least one", preferably "exactly one". Hence, for example, a plurality of working electrodes can of course also be coated, e.g. simultaneously, using the method.

By dint of the reference thereto, all the publications identified in the description are incorporated in full into the description. The present invention is explained below with reference to drawings which show examples and exemplary embodiments. These are intended to contribute to understanding but do not limit the scope of protection. In the drawings:

EXAMPLE 1

Figures 1A, 1B:
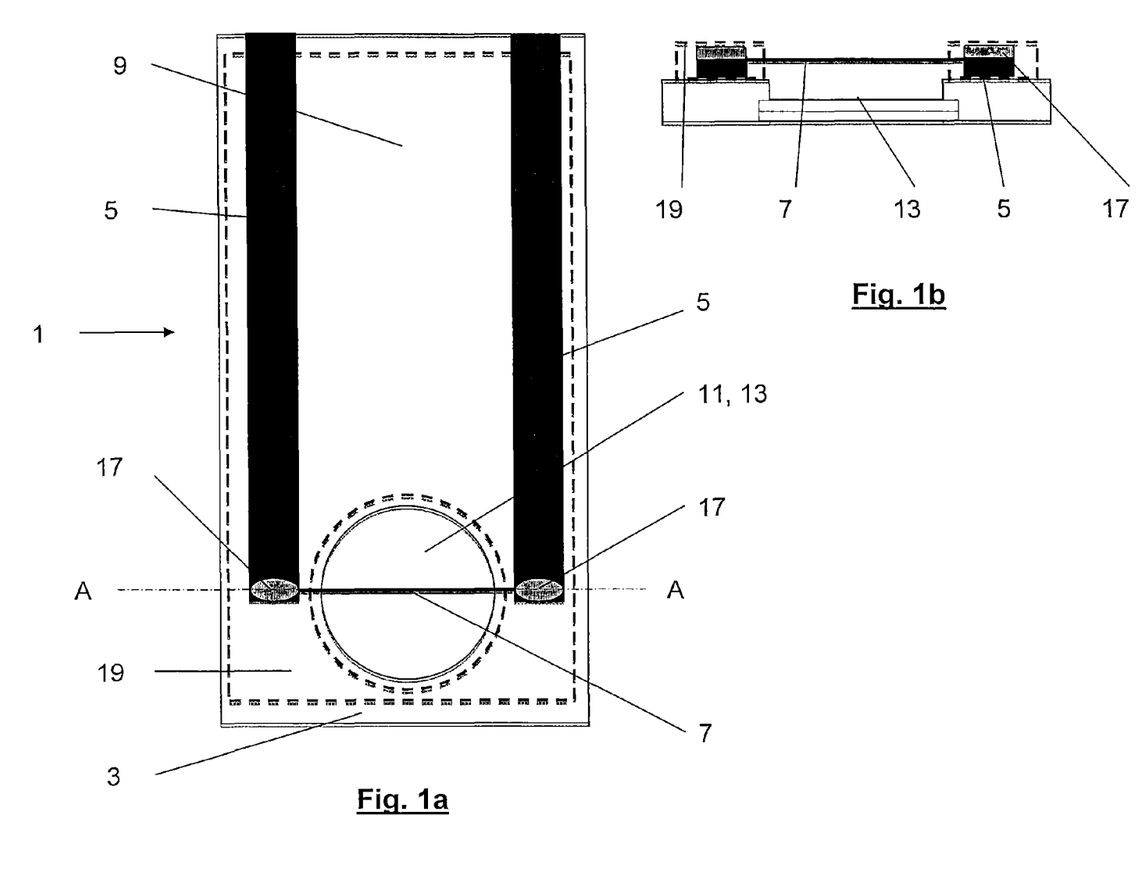
FIG. 1a shows a plan view of an exemplary embodiment of a sensor according to the invention.
FIG. 1b shows a section along the plane A-A of the exemplary embodiment from FIG. 1a, FIG. 2 shows a section along the plane A-A of the exemplary embodiment from FIG. 1a with a liquid drop in the recess.

An exemplary embodiment of the electrochemical sensor 1 is shown in FIG. 1. The electrochemical sensor 1 comprises a base element 3, a pair of conductors 5, and a wire-shaped working electrode 7. Further, the sensor optionally comprises a counter electrode 8a and a pseudo reference electrode 8b, the exact form of which, however, is not important for the present exemplary embodiment.

The base element 3 is made of electrically insulating material and has a planar surface 9. The two conductors 5 of a pair are superimposed on the planar surface 9 of the base element 3 and are connected to one another by means of the wire-shaped working electrode 7. Beneath the working electrode 7, the base element 3 has a recess 11 in the otherwise planar surface 9. The bottom 13 of this recess 11 is at a distance from the working electrode 7 so that the surface of the working electrode 7 is accessible along its whole circumference (see FIG. 2).

Figure 2:
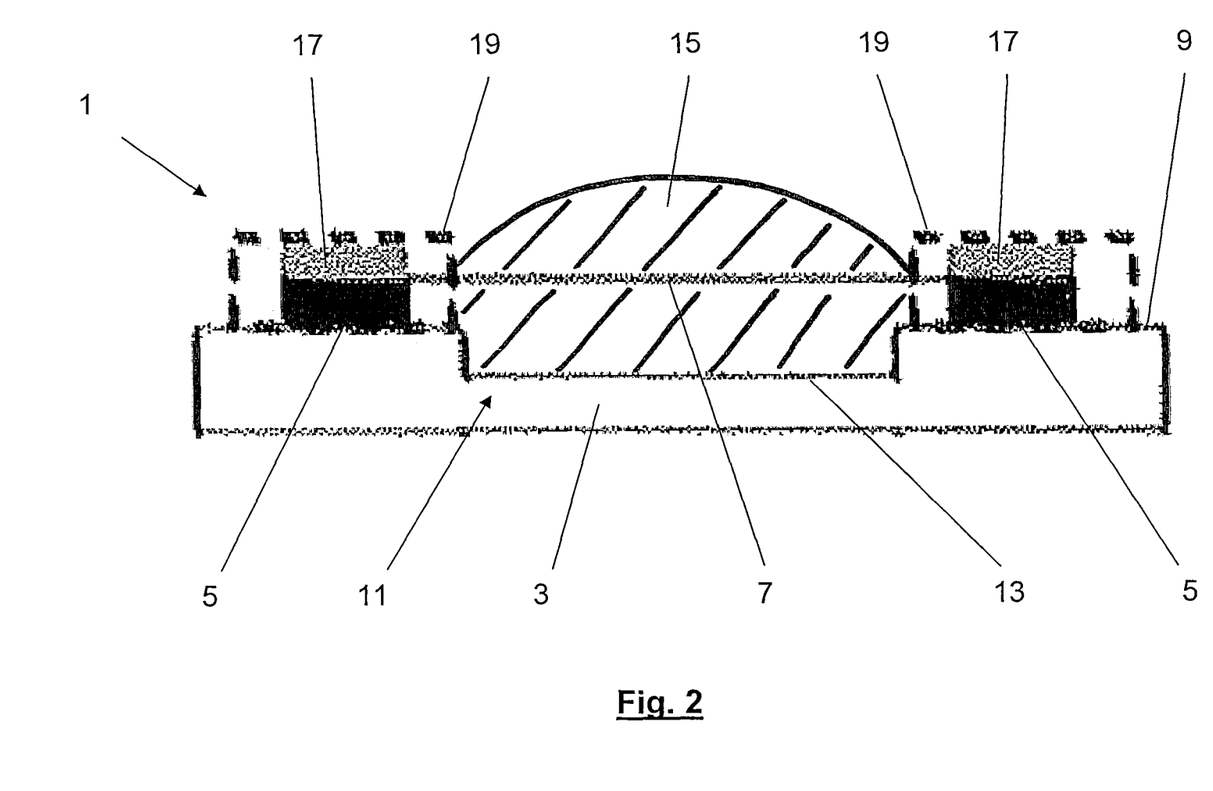

The recess 11 in the base element 3 beneath the working electrode 7 has a form which enables a liquid drop 15 to be accommodated therein, wherein the working electrode 7 is surrounded and wetted along its whole surface by the liquid of the liquid drop. The liquid drop is therefore not accommodated in the recess 11 with its full dimensions, but, facilitated by the surface tension of the liquid, projects beyond the plane of the surface 9 of the base element 3 and beyond the working electrode 7 which extends substantially in the plane of the planar surface 9 of the base element 3 so that the working electrode 7 passes through the liquid drop 15.

In the present exemplary embodiment, the liquid drop 15 has a volume of between 10 and 20 µL and the working electrode 7 has a length of 5 mm and a diameter of 25 µm. Here, the recess 11 has a circular form (see FIG. 1) and the bottom 13 of the recess 11 is planar and formed parallel to the planar surface 9 of the base element 3. In the exemplary embodiment described, the distance of the working electrode 7 from the bottom 13 of the recess 11 is 0.5 mm over the whole length of the working electrode 7.

Here, the working electrode 7 can be directly heated in order to guarantee an ideal temperature for bonding target molecules, e.g. to probe molecules at the surface of the working electrode 7. Directly heated is understood to mean that both the heating current and the electrochemical electrolysis current which represents the measuring signal (voltammetry, amperometry, coulometry) or which produces the measuring signal (chronopotentiometry) flow through the working electrode 7 itself. However, a symmetrical bridge circuit with 2 induction coils, as disclosed in the prior art, is used in order to obtain an unaffected measuring signal (not shown in the figures). The working electrode 7 and/or its contacts with the conductors 5 are designed such that a uniform temperature distribution is achieved at the surface of the working electrode 7.

Here, the working electrode 7 is formed by a wire with a substantially circular cross section. However, the cross section can likewise have a rectangular form, for example. The working electrode 7 preferably has a material from the series gold, silver, copper, platinum, iridium, palladium, bismuth, antimony or carbon, in particular gold or platinum, preferably gold. The working electrode 7 can be coated. For example, mercury, amalgam, bismuth, silver, gold or an alloy of these can be considered as the coating material. In addition, the working electrode 7 can be coated with micro and/or nanostructures. Galvanic silver or gold structures, carbon, nanotubes, fullerenes or graphenes can be considered for this purpose.

The working electrode 7 is connected to the conductors 5 by means of contact points 17. These contact points 17 have an electrically conductive material and are implemented here by means of solder connections. According to the present exemplary embodiment, the base element 3 is designed as a conventional single-side-printed circuit board and the conductors 5 are, as usual, designed as copper conductor tracks.

Here, conductors 5 and base element 3 or conductor tracks and printed circuit board, including the contact points 17 of the conductors 5 with the working electrode 7, are covered by an insulating layer 19 so that only the working electrode 7 itself is exposed to the environment. Of the components described, only the working electrode 7 can be wetted by the liquid when the base element 3 comes into contact with a liquid. This does not rule out that the counter electrode 8a and, if applicable, the pseudo reference electrode 8b can also be wetted by the liquid. Here, the insulating layer 19 is a laminating foil which is stable with regard to its form and insulation properties in a temperature range of 25° C. to 93° C., but can also be realized by hot sealing adhesive, epoxy resin, polyester resin, silicone adhesive, solder resist varnish, dope, paraffin, rubber, PVC, Duroplast, PU resin, PTFE, PE, PS, polycarbonate, glass oxides, nitrides or other organic or inorganic polymers, varnish-like, crystalline or amorphous materials.

EXAMPLE 2

Figures 3A, 3B:
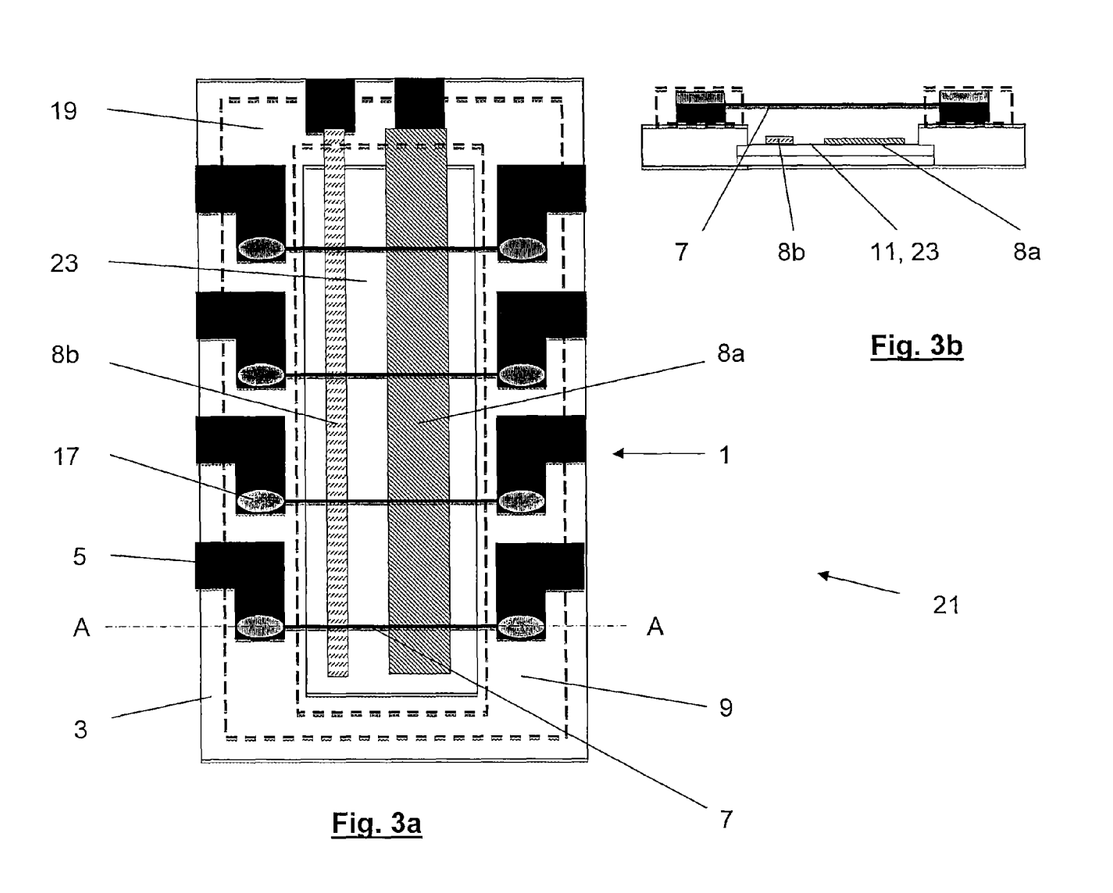
FIG. 3a shows a plan view on an exemplary embodiment of a sensor array according to the invention having a plurality of working electrodes, a counter electrode and a pseudo reference electrode.
FIG. 3b shows a section along the plane A-A of the exemplary embodiment from FIG. 3a, and FIG. 4 shows a section through an exemplary embodiment of a sensor according to the invention with a heat sink.

An exemplary embodiment of the sensor array 21 which relates to a further aspect of the present invention is shown in FIG. 3. The sensor array 21 has a plurality of previously described electrochemical sensors 1 according to the invention arranged behind one another, each having a pair of conductors 5 which are arranged on the planar surface 9 of a common base element 3 and which are connected to one another by a wire-shaped working electrode 7. Here, the individual sensors are arranged parallel and closely behind one another, i.e. both the working electrodes 7 and the conductors 5 run closely adjacent to one another, thus achieving a size of the sensor array 21 which is as small as possible.

Here, the individual recesses 11 of the sensor 1 in the base element 3 beneath the working electrode 7 are connected to form a common channel 23. Within the meaning of this exemplary embodiment, the working electrodes 7 can be formed from the same material or from different materials in each case. The coating of the working electrodes 7 can also be of the same material for all working electrodes 7 or be realized from different materials in each case. The materials of the working electrode 7 and its coating can be selected from the range of materials stated in conjunction with the electrochemical sensor 1. The same applies to the material of the base element 3 and the conductors 5.

The sensor array 21 is jointly covered by an insulating layer 19 in a similar way to the individual electrochemical sensor 1, so that, during an analysis, only the individual working electrodes 7 or, in addition, if applicable, a counter electrode and, if existing, a pseudo reference electrode 8a, 8b (see FIG. 3) can come directly into contact with a liquid which wets the sensor array 21. Here, as in the case of the individual sensor 1, the insulating layer 19 can be a laminating foil which is stable between 25° C. and 93° C.

Counter electrode 8*a* and, if applicable, reference electrode 8*b* can be arranged on the same base element 3 or separately therefrom. All working electrodes 7 of the exemplary embodiment described of the sensor array 21 can be directly heated independently of one another so that the various sensors 1 of the array 21 can come into contact with the liquid at an individual temperature, e.g. one which is optimum for a reaction. The direct heating is carried out as described previously for the individual sensor 1 with the help of a symmetrical bridge circuit.

EXAMPLE 3

A sensor array 21 according to example 2, in which working electrodes 7 made from the materials gold, platinum and silver are used, is used to be able to simultaneously determine (a) mercury on the gold wire, (b) arsenic (V) together with arsenic (III) on the gold wire, (c) arsenic (III) alone on the gold wire, (d) cadmium on the silver wire and (e) phenol derivatives on the platinum wire, in a sample solution. In doing so, use is made of the fact that the sensor array 21 can be selectively heated so that each working electrode 7 has its own time-dependent temperature profile. Mercury and arsenic can best be deposited on gold and determined by stripping analysis. Cadmium requires the relatively high hydrogen voltage on silver. Phenol bonds can only be oxidized at relatively high potentials; in addition, pulsed heating to high temperatures for cleaning the electrodes is necessary here, for which purpose platinum is most suitable.

EXAMPLE 4

The sensor according to example 1 or the sensor array according to example 2 or 3 is provided with a pseudo reference electrode 8*b* in such a way that a narrow gold or silver layer is located on the base element 3 beneath the electrode wire 7 (see FIG. 3). This ensures that the pseudo reference electrode 8*b* is located at the coldest point of the measuring cell where, in addition, the temperature and therefore the potential of the pseudo reference electrode 8*b* also remain constant. Preferably, the distance between working electrode 7 and pseudo reference electrode 8*b* is greater than 200 μm, and particularly preferably greater than 400 μm. This ensures that no troublesome heating of the pseudo reference electrode 8*b* takes place even due to heat conduction, (cf. FIG. 2 in J. Phys. Chem. B 2000, 104, 764-769).

In this example, the counter electrode 8*a* is formed by a second metallic layer (Pt or Au) or a carbon layer on the base element 3 which runs parallel to the pseudo reference electrode 8*b*. Here, platinum and gold can be deposited by sputtering or vapor deposition.

The counter electrode 8*a* can also be realized in the form of the underside of the metallic heat sink 25 (see FIG. 4) which, for example, is connected by means of a peripheral seal 27 to the insulating layer 19 of the sensor 1, wherein the particular advantage of the cooling effect and the large surface area are linked (cf. G.-U. Flechsig, J. Peter, DE 10 2005 007 148 B4, claims 17ff., FIG. 1).

Figure 4:
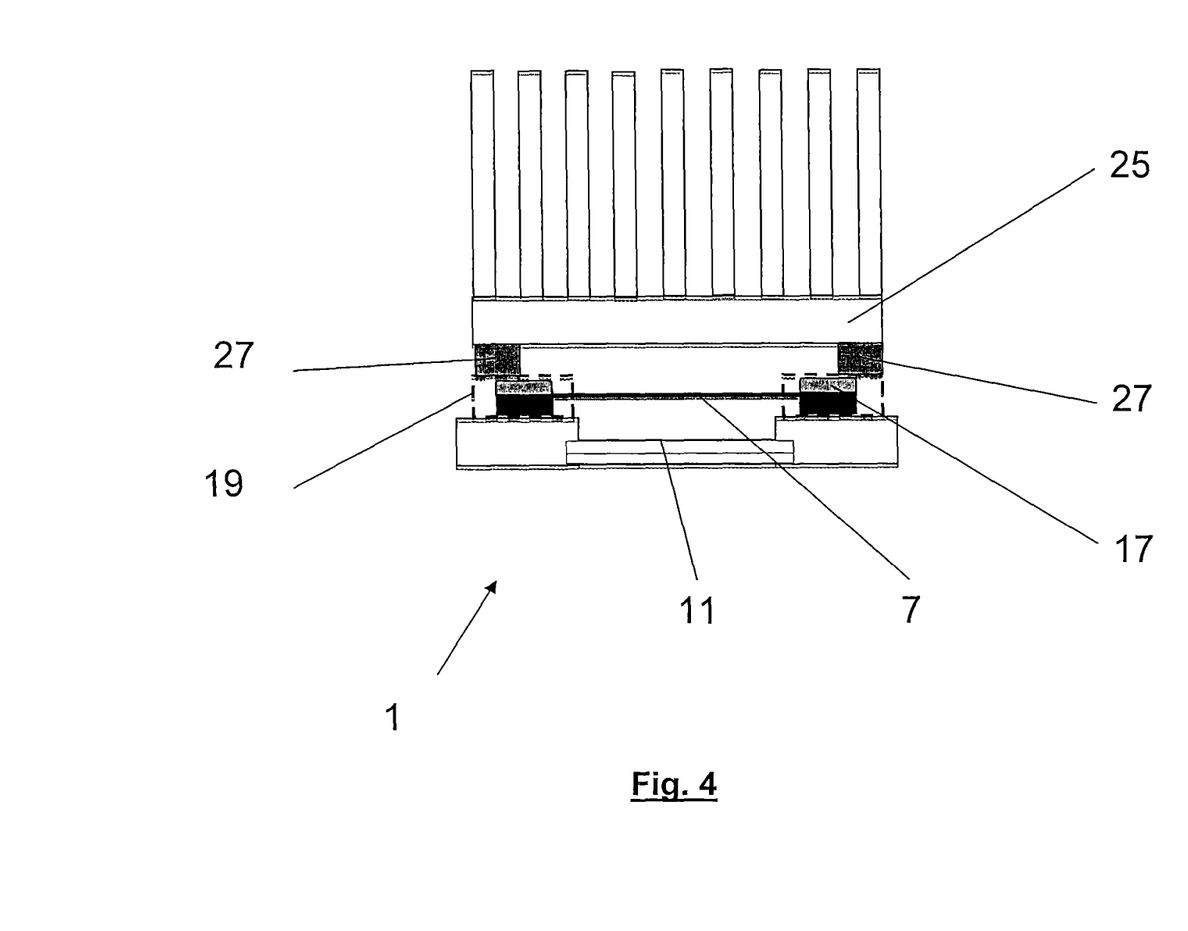

By this means, the quantity of liquid in the recess 11 is also protected and enclosed before evaporation.

EXAMPLE 5

In this example, a silicon chip is used as the base element 3 instead of a printed circuit board with printed copper conductor tracks. The metal conductor tracks can either be deposited by sputtering or vapor deposition. Alternatively, conductor tracks are incorporated into the silicon base element 3 by n or p-dosing. The working electrodes 7 are fixed to the conductor tracks by bonding or soldering. The recess is formed by etching with HF. Insulating layers 19 are to be realized particularly by means of silicon nitrides and silicon oxides.

The invention claimed is:

1. An electrochemical sensor element (1) having a base element (3) made of electrically insulating material with a planar surface (9), and a pair of conductors (5) which are superimposed on this planar surface (9) of the base element (3), wherein the two conductors (5) of the pair are connected by means of at least one wire-shaped working electrode (7), wherein a recess (11) is formed in the planar surface (9) of the base element (3) beneath the working electrode (7), wherein the bottom (13) of the recess (11) is at a distance from the working electrode (7).

2. The sensor element of claim 1, wherein the recess (11) is designed such that, when a liquid drop (15) is introduced into the recess (11), the working electrode (7) can be wetted by the liquid, wherein the whole surface of the working electrode (7) can be wetted.

3. The sensor element of claim 1, wherein the sensor element incorporates a liquid drop (15) which has contact with the working electrode (7) and with the bottom (13) of the recess (11).

4. The sensor element of claim 3, wherein the liquid drop (15) has a volume of 5 to 30 μL.

5. The sensor element of claim 1, wherein the working electrode (7) can be directly heated.

6. The sensor element of claim 1, wherein the conductors (5) and the contact points (17) of the conductor (5) with the working electrode (7) are covered by an insulating layer (19) on the sides which are not superimposed on the base element (3).

7. The sensor element of claim 1, wherein the base element (3) is a printed circuit board and the conductors (5) are in the form of conductor tracks, wherein the conductors (5) and the contact points (17) of the conductor (5) with the working electrode (7) are covered by an insulating laminating foil on the sides which are not superimposed on the base element (3).

8. The sensor element of claim 1, wherein the working electrode (7) has a length of 3 to 10 mm, and a diameter of 10 to 30 μm.

9. The sensor element of claim 1, wherein the bottom (13) of the recess (11) is designed to be planar and parallel to the planar surface (9) of the base element (3).

10. The sensor element of claim 1, wherein the distance of the working electrode (7) from the bottom (13) of the recess (11) at at least one point is 0.2 mm to 0.8 mm.

11. A sensor element array (21) which has two or more sensor elements (1) of claim 1, wherein the sensor elements (1) are arranged together on a base element (3).

12. The sensor element array of claim 11, wherein the recesses (11) beneath at least 2 working electrodes (7) are connected to one another to form a common channel (23).

13. The sensor element array of claim 11, wherein the working electrodes (7) are in each case made of the same material, wherein the material is selected from the group comprising gold, silver, copper, platinum, iridium, palladium, bismuth, antimony, mercury, carbon or combinations thereof.

14. The sensor element array of claim 11, having at least one of the sensor elements (1) with a heated working electrode (7), wherein the sensor element array (21) includes an unheated counter electrode (8a).

15. A method for coating a working electrode (7) comprising steps in which a liquid drop (15) of a coating liquid is introduced into a recess (11) of the sensor element (1) of claim 1 or the sensor element array (21) of claim 11.

16. The sensor element of claim 4, wherein the liquid drop (15) has a volume of 10 to 20 μL.

17. The sensor element of claim 5, wherein the sensor (1) is designed such that the temperature distribution at the surface of the working electrode (7) is uniform.

18. The sensor element of claim 6, wherein said insulating layer (19) is stable at least in a temperature range of 25° C. to 93° C.

19. The sensor element of claim 6, wherein said insulating layer (19) is a laminating foil.

20. The sensor element of claim 8, wherein the working electrode (7) has a length of 5 mm and a diameter of 25 μm.

21. The sensor element of claim 10, wherein the distance of the working electrode (7) from the bottom (13) of the recess (11) at at least one point is 0.5 mm.

22. The sensor element of claim 10, wherein the recess (11) extends over the whole length of the working electrode (7).

23. The sensor element array of claim 11, wherein the recesses (11) beneath at least 2 working electrodes (7) are separate from one another.

24. The sensor element array of claim 11, wherein the working electrodes (7) are in each case made of different materials, wherein the materials are selected from the group comprising gold, silver, copper, platinum, iridium, palladium, bismuth, antimony, mercury, carbon or combinations thereof.

25. The sensor element array of claim 14, having the two or more sensors elements (1) with heated working electrodes (7), wherein the heated working electrodes can be heated independently of one another in each case.

26. The sensor element array of claim 14, wherein the sensor element array (21) includes an unheated pseudo reference electrode (8b).

\* \* \* \* \*